(12) United States Patent
Washburn et al.

(10) Patent No.: US 7,589,193 B2
(45) Date of Patent: Sep. 15, 2009

(54) C-ARYL GLUCOSIDE SGLT2 INHIBITORS AND METHOD

(75) Inventors: William Washburn, Titusville, NJ (US); Wei Meng, Pennington, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 433 days.

(21) Appl. No.: 11/233,617

(22) Filed: Sep. 23, 2005

(65) Prior Publication Data

US 2006/0063722 A1    Mar. 23, 2006

Related U.S. Application Data

(60) Provisional application No. 60/612,599, filed on Sep. 23, 2004.

(51) Int. Cl.
    C07H 7/04 (2006.01)
(52) U.S. Cl. .......................... 536/122; 514/23
(58) Field of Classification Search ................. 536/122; 514/23; C07H 7/04, 7/06
    See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauey et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,346,701 A | 9/1994 | Heiber et al. |
| 5,354,772 A | 10/1994 | Kathawala |
| 5,385,929 A | 1/1995 | Bjorge et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,595,872 A | 1/1997 | Wetterau et al. |
| 5,612,359 A | 3/1997 | Murugesan |
| 5,614,492 A | 3/1997 | Habener |
| 5,631,224 A | 5/1997 | Efendic et al. |
| 5,686,104 A | 11/1997 | Mills et al. |
| 5,691,322 A | 11/1997 | Robl |
| 5,712,279 A | 1/1998 | Biller et al. |
| 5,712,396 A | 1/1998 | Magnin et al. |
| 5,739,135 A | 4/1998 | Biller et al. |
| 5,753,675 A | 5/1998 | Watanasin |
| 5,760,246 A | 6/1998 | Biller et al. |
| 5,770,615 A | 6/1998 | Cheng et al. |
| 5,776,983 A | 7/1998 | Washburn et al. |
| 5,827,875 A | 10/1998 | Dickson, Jr. et al. |
| 5,885,983 A | 3/1999 | Biller et al. |
| 5,962,440 A | 10/1999 | Sulsky |
| 6,043,265 A | 3/2000 | Murugesan et al. |
| 6,395,767 B2 | 5/2002 | Robl et al. |
| 6,414,126 B1 * | 7/2002 | Ellsworth et al. .......... 536/17.2 |
| 6,548,529 B1 | 4/2003 | Robl et al. |
| 6,653,314 B2 | 11/2003 | Cheng et al. |
| 7,393,836 B2 * | 7/2008 | Eckhardt et al. ............... 514/23 |
| 7,419,959 B2 * | 9/2008 | Eckhardt et al. ............... 514/23 |
| 2006/0128635 A1 * | 6/2006 | Fujikura et al. ................ 514/23 |
| 2006/0142210 A1 * | 6/2006 | Eckhardt et al. ............... 514/25 |
| 2008/0182802 A1 * | 7/2008 | Hadd et al. .................... 514/27 |
| 2008/0234367 A1 * | 9/2008 | Washburn et al. ........... 514/460 |
| 2008/0242596 A1 * | 10/2008 | Chen et al. ....................... 514/4 |

FOREIGN PATENT DOCUMENTS

| | | |
|---|---|---|
| EP | 0 221 025 | 5/1987 |
| EP | 0 142 146 | 8/1988 |
| FR | 2 596 393 | 10/1987 |
| GB | 2 205 837 | 12/1988 |
| WO | WO 86/03488 | 6/1986 |

(Continued)

OTHER PUBLICATIONS

Mizuma et al. Biochimica et Biophysica Acta, 1998, 1381, p. 340-346.*

(Continued)

*Primary Examiner*—Shaojia Anna Jiang
*Assistant Examiner*—Jonathan S Lau
(74) *Attorney, Agent, or Firm*—Maureen S. Gibbons; Burton Rodney

(57) ABSTRACT

A compound of the formula I

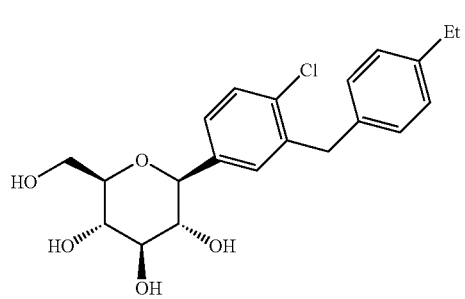

A method is also provided for treating diabetes and related diseases employing the above compound alone or in combination with another therapeutic agent.

15 Claims, No Drawings

FOREIGN PATENT DOCUMENTS

| WO | WO 86/07054 | 12/1986 |
| --- | --- | --- |
| WO | WO 97/12613 | 4/1997 |
| WO | WO 97/12615 | 4/1997 |
| WO | WO 97/21993 | 6/1997 |
| WO | WO 99/00353 | 1/1999 |
| WO | WO 99/38501 | 8/1999 |
| WO | WO 99/46272 | 9/1999 |
| WO | WO 96/38144 | 12/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | WO 01/21602 | 3/2001 |
| WO | WO 01/27128 | 4/2001 |
| WO | WO 01/68603 | 9/2001 |
| WO | WO 02/083066 | 10/2002 |
| WO | WO 03/033671 | 4/2003 |
| WO | WO 03/099836 | 12/2003 |
| WO | WO 2004031203 | * 4/2004 |
| WO | WO 2004/063209 | 7/2004 |

OTHER PUBLICATIONS

Ashworth, D. M., et al., "2-Cyanopyrrolidides As Potent, Stable Inhibitors Of Dipeptidyl Peptidase IV", Bioorganic & Medicinal Chemistry Letters, vol. 6(10), pp. 1163-1166, (1996).

Ashworth, D. M., et al., "4-Cyanothiazolidides As Very Potent, Stable Inhibitors of Dipeptidyl Peptidase IV", Bioorganic & Medicinal Chemistry Letters, vol. 6(22), pp. 2745-2748, (1996).

Avasimibe, "Treatment of Lipoprotein Disorders ACAT Inhibitor", Drugs of the Future, vol. 24(1), pp. 9-15, (1999).

Biller, S. A, et al., "Isoprenoid (Phosphinylmethyl) Phosphonates as Inhibitors of Squalene Synthetase", Journal of Medicinal Chemistry, vol. 31(10), pp. 1869-1871, (1988).

Biller, S.A. et al., "Squalene Synthase Inhibitors", Current Pharmaceutical Design, vol. 2(1)V, pp. 1-40 (1996).

Bundgaard, H., Chapter 5: "Design and Application of Prodrugs", A Textbook of Drug Design and Development, Harwood Academic Publishers, publ., Krogsgaard-Larsen, P. et al., eds., pp. 113-191 (1991).

Bundgaard, H., ed., Design of Prodrugs, Elsevier Science Publishers B.V., publ. (1985) (table of contents).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Corey, E. J. et al., "Application of Unreactive Analogs of Terpenoid Pyrophosphates to Studies of Multistep Biosynthesis. Demonstration That "Presqualene Pyrophosphate" Is an Essential Intermediate on the Path to Squalene", Journal of American Chemistry Society, vol. 98, pp. 1291-1293, (1976).

Cornicelli, J. A., et al., "15-Lipoxygenase and Its Inhibition: A Novel Therapeutic Target for Vascular Disease", Current Pharmaceutical Design, vol. 5, pp. 11-20, (1999).

Evans, H. J., "Cytological Methods for Detecting Chemical Mutagens", Chemical mutagens, principals and methods for their detection, Chapter 35, vol. 4, pp. 1-29, (1976).

Galloway, S. M., "Cytotoxicity and Chromosome Aberrations In Vitro: Experience in Industry and the Case for an Upper Limit on Toxicity in the Aberration Assay", Environmental and Molecular Mutagenesis, vol. 35, pp, 191-201, (2000).

Galloway, S. M., et al., "Report From Working Group On In Vitro Tests for Chromosomal Aberrations", Mutation Research, vol. 312, pp. 241-261, (1994).

Galloway, S.M., et al., "Development of a Standard Protocol for In Vitro Cytogenetic Testing with Chinese hamster Ovary Cells: Comparison of Results for 22 Compounds in two Laboratories", Environmental Mutagenesis, vol. 7, pp. 1-51, (1985).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Hara, S., "Ileal $Na^+$/bile acid Contransporter inhibitors", Drugs of the Future, vol. 24(4), pp. 425-430, (1999).

Hilliard, C. A., et al., "Chromosome Aberrations In Vitro Related to Cytotoxicity of Nonmutagenic Chemicals and Metabolic Poisons", Environmental and Molecular Mutagenesis, vol. 31, pp. 316-326, (1998).

Hughes, T. E., et al., (1-[[[2-[(5-Cyanopyridin-2-yl)amino]amino]ethyl]amino]acetyl) -2-cyano-(S)-Pyrrolidine), a Slow-Binding Inhibitor of Dipeptidyl Peptidase IV, Biochemistry, vol. 38, pp. 11597-11603, (1999).

Johnnsson, G., et al., "Growth Hormone Treatment of Abdominally Obese Men Reduces Abdominal Fat Mass, Improves Glucose and Lipoprotein Metabolism, and Reduces Diastolic Blood Pressure", vol. 82(3), pp. 727-734, (1997).

Krause, B.R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R.R. et al., eds., pp. 173-198 (1995).

Preston, R. J., et al., Mammalian in vivo and in vitro cytogenetic assay: A report of the U.S. EPA's Gene-Tox Program[1], vol. 87, pp. 143-188, pp. 1981.

Ortiz de Montellano, P. R., "Inhibition of Squalene Synthetase by Farnesyl Pyrophosphate Analogues[1]", Journal of Medicinal Chemistry, vol. 20(2), pp. 243-249, (1977).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Murakami, K., et al., A Novel Insulin Sensitizer Acts as a Coligand for Peroxisome Proliferator-Activated Receptor-α (PPAR-α) and PPAR-γ), Diabetes, vol. 47, pp. 1841-1847, (1998).

Nicolosi, R. J., et al., "The ACAT inhibitor, CI-1011 is effective in the prevention and regression of aortic fatty streak area in hamsters", Atherosclerosis, vol. 137, pp. 77-85, (1998).

Rosenblum, S. B., et al., "Discovery of 1-(4-Fluorophenyl)-3R)-[3-(4-fluorophenyl)-(3S)-hydroxypropyl]-4S)-4-hydroxyphenyl)-2-azetidinone (SCH 58235): A Designed, Potent, Orally Active Inhibitor of Cholesterol Absorption", J. Med. Chem., vol. 41, pp. 973-980, (1998).

Salisbury, B. G., et al., "Hypocholesterolemic activity of a novel inhibitor of cholesterol absorption, SCH 48461", Atherosclerosis, vol. 115, pp. 45-63, (1995).

Scott, D., et al., "In Vitro Chromosome Aberration Assay", UKEMS Sub-Committee on Guidelines for Mutagenicity Testing, The United Kingdom Environmental Mutagen society Chapter 3, pp. 41-64, (1983).

Sendobry, S. M., et al., "Attenuation of diet-induced atherosclerosis in rabbits with a highly selective 15-lipoxygenase inhibitor lacking significant antioxidant properties", British Journal of Pharmacology, vol. 120, pp. 1199-1206, (1997).

Sliskovic, D.R. et al., "ACAT Inhibitors: Potential Anti-atherosclerotic Agents", Current Medicinal Chemistry, vol. 1, No. 3, pp. 204-225 (1994).

Smith, C., et al., RP73163: A Bioavailable Alkylsulphinyl-Diphenylimidazole ACAT Inhibitor[1], Bioorganic & Medicinal Chemistry Letter, vol. 6(1), pp. 47-50, (1996).

Snyder, R. D., et al., "A review of the genotoxicity of marketed pharmaceuticals", Mutation Research, vol. 488, pp. 151-169, (2001).

Stout, D.M., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity, etc.", Chemtracts-Organic Chemistry, vol. 8, pp. 359-362 (1995).

Swierenga, S.H.H. et al., "Recommended protocols based on a survey of current practice in genotoxicity testing laboratories, IV. Chromosome aberration and sister-chromatid exchange in Chinese hamster ovary, V79 Chinese hamster lung and human lymphocyte cultures", Mutation Research, vol. 246, pp. 301-322, (1991).

Wermuth, C.G. et al., Chapter 31: "Designing Prodrugs and Bioprecursors I: Carrier Prodrugs", The Practice of Medicinal Chemistry, Academic Press Limited, publ., Wermuth, C.G., ed., pp. 671-696 (1996).

Yamada, M., et al., "A Potent Dipeptide Inhibitor of Dipeptidyl Peptidase IV", Bioorganic & Medicinal Chemistry Letters, vol. 8, pp. 1537-1540, (1998).

* cited by examiner

C-ARYL GLUCOSIDE SGLT2 INHIBITORS AND METHOD

CROSS-REFERENCE TO RELATED APPLICATIONS

This application claims the priority benefit of U.S. Provisional Application No. 60/612,599, filed Sep. 23, 2004, the disclosure of which is incorporated herein by reference in its entirety.

FIELD OF THE INVENTION

The present invention relates to C-aryl glucosides which are selective inhibitors of sodium dependent glucose transporters found in the kidney and to a method for treating diabetes or disorders by employing such C-aryl glucosides alone or in combination with one or more other type of therapeutic agent

BACKGROUND OF THE INVENTION

Approximately 100 million people worldwide suffer from type II diabetes (NIDDM), which is characterized by hyperglycemia due to excessive hepatic glucose production and peripheral insulin resistance, the root causes for which are as yet unknown. Consistent control of plasma glucose levels in diabetes patients may offset the development of diabetic complications and beta cell failure seen in advanced disease.

Plasma glucose is normally filtered in the kidney in the glomerulus and actively reabsorbed in the proximal tubule. Ninety percent of glucose reuptake in the kidney occurs in the epithelial cells of the early S1 segment of the renal cortical proximal tubule. SGLT2, a 672 amino acid protein containing 14 membrane-spanning segments that is predominantly expressed in the early S1 segment of the renal proximal tubules, is likely to be the major transporter responsible for this reuptake. The substrate specificity, sodium dependence, and localization of SGLT2 are consistent with the properties of the high capacity, low affinity, sodium-dependent glucose transporter previously characterized in human cortical kidney proximal tubules. In addition, hybrid depletion studies implicate SGLT2 as the predominant $Na^+$/glucose cotransporter in the S1 segment of the proximal tubule, since virtually all Na-dependent glucose transport activity encoded in mRNA from rat kidney cortex is inhibited by an antisense oligonucleotide specific to rat SGLT2. In humans, mutations in SGLT2 have been associated with familial forms of renal glucosuria, providing further evidence of the primary role of SGLT2 in renal glucose reabsorption. In such patients, renal morphology and renal function is otherwise normal. Inhibition of SGLT2 would be predicted to reduce plasma glucose levels via enhanced glucose excretion in diabetic patients.

SGLT1, another Na-dependent glucose cotransporter that is 60% identical to SGLT2 at the amino acid level, is expressed in the small intestine and in the more distal S3 segment of the renal proximal tubule. Despite their sequence similarities, human SGLT1 and SGLT2 are biochemically distinguishable.

Administration of phlorizin, a specific inhibitor of SGLT activity, provided proof of concept in vivo by promoting glucose excretion, lowering fasting and fed plasma glucose, and promoting glucose utilization without hypoglycemic side effects in several diabetic rodent models and in one canine diabetes model. No adverse effects on plasma ion balance, renal function or renal morphology have been observed as a consequence of phlorizin treatment for as long as two weeks.

In addition, no hypoglycemic or other adverse effects have been observed when phlorizin is administered to normal animals, despite the presence of glycosuria. Administration of an inhibitor of renal SGLTs for a 6-month period (Tanabe Seiyaku) was reported to improve fasting and fed plasma glucose, improve insulin secretion and utilization in obese NIDDM rat models, and offset the development of nephropathy and neuropathy in the absence of hypoglycemic or renal side effects.

General inhibitors of SGLT 1 & 2 activity are unattractive therapeutically because inhibition of SGLT1 could also have serious adverse consequences as is illustrated by the hereditary syndrome glucose/galactose malabsorption (GGM), in which mutations in the SGLT1 cotransporter result in impaired glucose uptake in the intestine, and life-threatening diarrhea and dehydration. Selective inhibition of SGLT2 in diabetic patients would be expected to normalize plasma glucose by enhancing the excretion of glucose in the urine, thereby improving insulin sensitivity, and delaying the development of diabetic complications, in the absence of significant gastrointestinal side effects.

Accordingly, the discovery of compounds that are selective to the SGLT2 transporter may demonstrate a utility for the treatment or prevention of diseases or disorders associated with control of plasma glucose levels, such as diabetes.

SUMMARY OF THE INVENTION

In accordance with the present invention, a C-aryl glucoside compound is provided having the structure

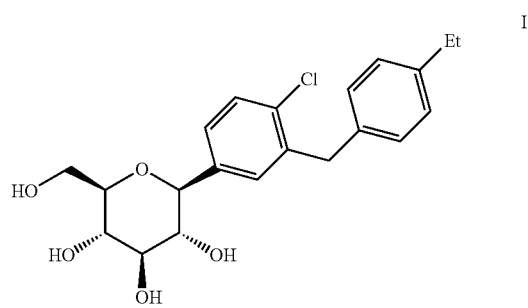

The compound of formula I includes pharmaceutically acceptable salts, complexes, stereoisomers, and prodrug esters thereof.

The compound of formula I possesses activity as a selective inhibitor of SGLT2 and therefore may provide utility for the prevention or treatment of diseases or disorders associated with the control of plasma glucose levels. Examples of such diseases or disorders include diabetes and the micro- and macrovascular complications of diabetes.

The present invention provides for a compound of formula I, pharmaceutical compositions employing such a compound and for methods of using such a compound. In particular, the present invention provides a pharmaceutical composition comprising a therapeutically effective amount of a compound of formula I, alone or in combination with a pharmaceutically acceptable carrier.

In addition, in accordance with the present invention, a method is provided for treating or delaying the progression or onset of the diseases or disorders described herein, wherein a therapeutically effective amount of a compound of formula I is administered to a human patient in need of treatment.

The compound of the invention can be used alone, or in combination with one or more other agent(s) active in the therapeutic areas described herein.

Further, a method is provided for treating the diseases as defined above and hereinafter, wherein a therapeutically effective amount of a compound of formula I and another type of antidiabetic agent and/or another type of therapeutic agent, such as a hypolipidemic agent, is administered to a human patient in need of treatment.

DETAILED DESCRIPTION OF THE INVENTION

The following chart contains a matrix comparison of the compound of the invention (compound 1, column 4) to compounds of similar structure taking into consideration several characteristics relating to compound utility and commercial viability. The structures of compounds 1 (the compound of the invention) and 3-5, are illustrated below.

| Protocol | Property | Compound Number | | | |
|---|---|---|---|---|---|
| | | 5 | 4 | 3 | 1 (I) |
| A | % Decrease of plasma glucose in STZ diabetic rats at 5 hr after an oral dose of 0.1 mg/kg vs. vehicle treated controls | 34% | 60% | 59% | 62% |
| B | Stability in a prototypical formulation | Yes | Yes | No | Yes |
| C | In vitro clastogenic activity | Yes | Yes | — | No |

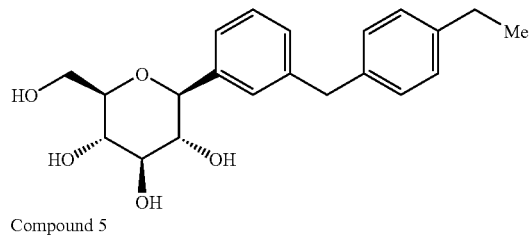

Compound 5

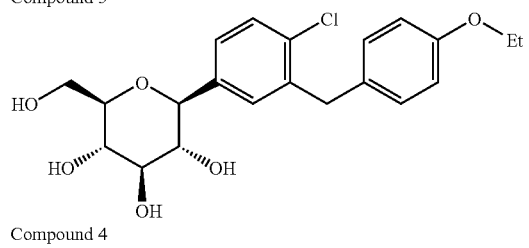

Compound 4

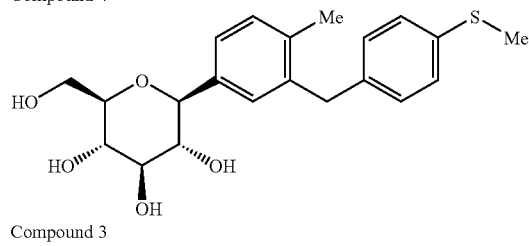

Compound 3

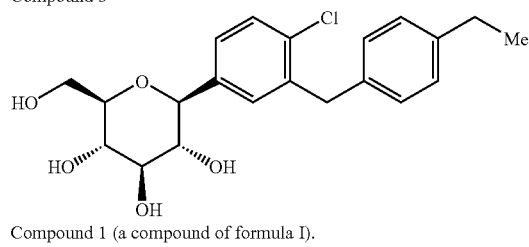

Compound 1 (a compound of formula I).

As illustrated in the chart above, only compound of formula I demonstrate favorable characteristics in all of the categories tested. That is, only compound of formula I demonstrate a favorable reduction of plasma glucose in diabetic rats (potency), stability in prototypic formulation (shelflife indication) and negative results in vitro clastogenic activity studies (reduced oncogenic potential).

Individual Protocol for Comparison Studies

I. Protocol for Study A: Determination of Blood Glucose Effect in Streptozotocin-Treated Diabetic Rats The following analysis was utilized to reasonably predict the impact on plasma glucose for the compounds analyzed in the matrix above.

Male Sprague Dawley rats (Charles River) weighing 250-275 g were made diabetic by a single intraperitoneal injection of streptozotocin (Sigma) at 65 mg/kg, prepared in fresh cold (4° C.) 0.01 M citrate buffer. Four days later, animals were bled in the fed state. Whole blood was collected via the tail tip and analyzed for glucose by the glucose oxidation method with a Glucometer Elite (Bayer). Mean blood glucose levels ranged from 450-550 mg/dl.

On the day of the experiment, the compound was dissolved in the vehicle comprised of 5% m-Pyrol, 20% PEG 400 and 20 mM Sodium Diphosphate. Rats were weighed, randomized into 4 groups with 6 rats in each group, and dosed orally with the vehicle or 0.1 mg/kg of the compound. The total volume for oral gavage was 1 ml/kg body weight. After dosing, the food was removed from the cages and the rats had access to water ad lib during the experiment. Blood samples were obtained from the tail tip at 0, 30, 60, 120, 180, 240 and 300 minutes following drug administration. Blood glucose was analyzed by the glucose oxidation method with a Glucometer Elite (Bayer).

A. Statistical Data Analysis

The calculation of mean blood glucose values and percent changes vs. vehicle at each time point were performed using Microsoft Excel. Statistical analyses (T tests, or ANOVA followed by Fisher's test) comparing drug-treated groups vs. vehicle controls) were performed using Microsoft Excel or the statistical program StatView. A p value of less that 0.05 was considered to be statistically significant.

II. Protocol for Study B: Stability Determination of Oxidatively Labile Therapeutic Agent in Presence of Commonly Used Solid Excipients, Under Accelerated Aging Conditions The following procedure was utilized to access the chemical stability of the compound 3 in the presence of commonly used excipients and typical antioxidants.

The drug substance was triturated in a mortar pestle with the respective antioxidant, and then mixed in the dry state with other excipients listed in the following table. Sodium metabisulfite and butylated hydroxyl anisole (BHA) were used as antioxidants in this study. BHA was used at two levels, 0.01% w/w and 0.5% w/w, and sodium metabisulfite was used at 0.01% w/w. For samples stored at 40° C./73% RH and HIL/uv, oxygen gas was purged into the vials and they were tightly capped. The drug-excipient blends (A-D) were placed under the different accelerated aging conditions listed within the second table for 1 and 3 weeks prior to HPLC analysis. Compounds that did not have any apparent oxidative instability issues (compounds 1, 4 and 5) were found to be chemically stable in the presence of excipients that are commonly used in solid dosage forms.

TABLE 1

Common Excipients in the Presence and Absence
of Antioxidants Employed during Stability Evaluations
of Prototype Drug-Excipient Blends

| | Drug Excipient Blend (% w/w) | | | |
|---|---|---|---|---|
| Ingredient | A | B | C | D |
| Compound 3 | 12.9 | 12.9 | 12.9 | 12.9 |
| Lactose hydrous | 59.6 | 21.4 | 59.6 | 21.4 |
| Microcrystalline cellulose | 20.0 | 42.7 | 20.0 | 42.7 |
| PVP | 5.0 | — | 5.0 | — |
| Pregelatinized starch | — | 20.0 | — | 20.0 |
| CrospovidoneXL-10 | 2.0 | — | 2.0 | — |
| Sodium starch glycolate | — | 2.0 | — | 2.0 |
| Magnesium stearate | 0.5 | — | 0.5 | — |
| Silicon dioxide | — | 0.5 | — | 0.5 |
| Sodium stearyl fumarate | — | 0.5 | — | 0.5 |
| Antioxidant | 0.01 | 0.01 | — | — |

TABLE 2

Conditions for Stability Studies of Drug Excipient
Blends under Accelerated Aging Conditions

| Condition | Time weeks |
|---|---|
| | 0 |
| 5° C. (closed) | 1 |
| | 3 |
| 25° C./60% RH (closed) | 1 |
| | 3 |
| 40° C./75% RH—O$_2$— (closed) | 1 |
| | 3 |
| 25° C. —O$_2$-HIL/uv (closed) | 1 |
| | 3 |

III. Protocol for Study C: Cytogenetics Study in Chinese Hamster Ovary Cells

Early identification of potential therapeutic agents that could be oncogenic in man is highly desirable. In vitro clastogenicity studies provide one early indication of the potential carcengenicity of a compound[1]. The following protocol was utilized to predict the in vitro clastogenicity activity of compounds of therapeutic interest.

Clastogenicity was predicted by determining the potential of compounds of interest to induce structural chromosome damage in Chinese hamster ovary (CHO) cells. If the chromosome damage is significantly elevated beyond the background level, this is evidence that compound has clastogenic potential. The detection of a significantly elevated level of chromosome damage in this assay is considered an indicator of genetic damage.

A. Test Article Carrier and Control Articles

The vehicle control is dimethyl sulfoxide (DMSO). The positive controls were Mitomycin C for the 3-hr and 20-hr exposure without S9 activation and cyclophosphamide for the 3-hr exposure with S9 rat-liver enzymes. Both Mitomycin C and cyclophosphamide were diluted with sterile water.

B. Administration of the Compound of Interest Concentration Selection

Two stock solutions in DMSO of the compound of interest were prepared—one being a high concentration, the other low. Aliquots of the vehicle control, low and high dosing solutions were collected following treatment of the CHO cells and subsequently analyzed to determine the concentration of the compound of interest. The concentrations selected were based on the results of a non-GLP solubility/miscibility/range-finding cytotoxicity (ATP) assay with the compound of interest. Once the upper limit of solubility of the compound of interest was determined in DMSO, that DMSO solution is added to culture medium to determine effects on pH or osmmolality. Eleven concentrations of the compound of interest were tested in the range-finding cytotoxicity assay both in the presence (3 hr) and absence (20 hr) of rat-liver (S9) enzymes. The highest concentration tested was 10 mM, 5000 µg/ml, or the limits of solubility. Based on the solubility/miscibility/range-finding cytotoxicity (ATP) assay results, six concentrations were selected for testing in the full cytogenetics study.

Test Article Concentrations

The DMSO stock solution of the compound of interest was 100× concentration of the highest test-article concentration to be used in the full assay. Six concentrations are tested. The cytotoxicity dose response observed in the range finding study determined the serial dilution factor for the five lower doses. A total dosing volume of 50 µl (stock solution plus DMSO) is added to 5 ml of culture medium for all treatment groups.

Experimental Design

Duplicate cultures will be used for each treatment group. The experimental design was as follows:

| | Flask I.D. | | | Dosing | |
|---|---|---|---|---|---|
| Treatment Group | 3 hr with S9 | 3 hr without S9 | 20 hr without S9 | Solution Concentration (mg/ml) | Final Nominal Concentration (µg/ml) |
| DMSO | 1-2 | 17-18 | 33-34 | — | — |
| Conc. A of Cmpd. of interest | 3-4 | 19-20 | 35-36 | — | — |
| Conc. B of Cmpd. of interest | 5-6 | 21-22 | 37-38 | — | — |
| Conc. C of Cmpd. of interest | 7-8 | 23-24 | 39-40 | — | — |
| Conc. D of Cmpd. of interest | 9-10 | 25-26 | 41-42 | — | — |
| Conc. E of Cmpd. of interest | 11-12 | 27-28 | 43-44 | — | — |
| Conc. F of Cmpd. of interest | 13-14 | 29-30 | 45-46 | — | — |
| Mitomycin C | — | 31-32 | — | 0.01 | 0.1 |
| Mitomycin C | — | — | 47-48 | 0.005 | 0.05 |
| Cyclophosphamide | 15-16 | — | — | 1 | 10 |

D. Test System

The CHO cell line was derived from an ovarian biopsy of a female Chinese hamster. Cells used in this assay (CHO-WBL) were originally obtained from the laboratory of Dr. S. Wolff, University of California, San Francisco. The cells have since been subcloned to maintain karyotypic stability. This cell line has an average cycle time of 12 to 14 hours with a modal chromosome number of 21. The cells are routinely monitored for karyotype stability and potential mycoplasma contamination.

E. Identification

All culture flasks and/or tubes used in the study were labeled numerically. Centrifuge tubes for cell harvest, hypotonic treatment, and fixation were labeled with the identical number as the corresponding flask. Additionally, microscope slides prepared from the fixed cells bared the same number as the centrifuge tube. Microscope slides were coded by an independent observer for an unbiased-cytogenetic analysis for chromosome aberrations. Permanent labels were affixed to the coded slides.

F. Experimental Methodology

The chromosome aberration assay was conducted using standard procedures[2-6] by exposing cultures of CHO cells to a minimum of four concentrations of the test article as well as to the positive and vehicle controls. In the non-activated test system, treatment was for approximately 3 hr and for 20 hr and in the S9 activated test system, exposure was for 3 hr.[7,8]

S9 Metabolic Activation

The exogenous metabolic-activation (S9) system consisted of an Aroclor 1254-induced rat-liver S9 (post-mitochondrial) fraction, as well as salts and cofactors. The final concentration of S9, salts, and cofactors in exogenous metabolic-activation (S9) system was 10 μl/ml (1% v/v) Aroclor 1254-induced rat-liver S9 (post-mitochondrial) fraction, 2.5 mM $MgCl_2.6H_2O$, 1.25 mM glucose-6-phosphate, 10.3 mM KCl, 1 mM NADP, and 12.8 mM $Na_2HPO_4$ Preparation of Target Cells Exponentially growing CHO-WBL cells were seeded in McCoy's 5A medium supplemented with 10% fetal-bovine serum, L-glutamine (2 mM), penicillin G (100 units/ml), and streptomycin (100 g/ml) at approximately $0.5 \times 10^6$ cells/25 cm² flask. The flasks were incubated at approximately 37° C. in a humidified atmosphere of approximately 5% $CO_2$ in air for 16-24 hr.

Treatment of Target Cells

On the day after culture initiation, the culture medium was replaced with fresh medium. For the 3- and 20-hr exposures without metabolic activation, the dosing is done in the complete medium described above. For the 3-hr exposures, in the presence of S9 metabolic activation, the medium is identical to that as described above, except that it lacks the fetal-bovine serum and contains the S9, salts and cofactors. After the 3-hr treatment with and without metabolic activation, medium was aspirated, the cells rinsed with phosphate buffer saline, refed with complete medium and returned to the incubator.

Collection of Metaphase Cells

A single harvest time of approximately 20 hr from the initial treatment was used. This harvest time corresponds to approximately 1.5 times a cell cycle of approximately 13 hr.[8] Colcemid® will be added to the cultures at a final concentration of 0.1 μg/ml, 2-3 hr prior to cell harvest.

Cells were harvested by trypsinization, collected by centrifugation and an aliquot was removed to determine the cell counts and percent viable cells. The cell count and percent viability was used to determine cell growth inhibition relative to the vehicle control (cytotoxicity). The remainder of the cells were swollen with 0.075 M KCl, washed with three consecutive changes of fixative (methanol:glacial acetic acid, 3:1 v/v), capped and stored overnight or longer at approximately 2-8° C. To prepare slides, the cells were collected by centrifugation and resuspended in fresh fixative. The suspension of fixed cells were applied to glass microscope slides and air-dried. The slides were stained with Giemsa and permanently mounted.

G. Chromosome Aberration Analysis

Based on the observed cytotoxicity, a minimum of three concentrations was selected for chromosome aberration analysis. Generally, concentrations that reduce the cell count or mitotic index by >50% were not evaluated for chromosome aberrations, since there is evidence that excessive cytotoxicity can induce chromosome aberrations that are unrelated to a direct clastogenic effect of the test article.[9,10] A minimum of 500 cells from each slide and two slides per flask was evaluated for the frequency of cells in mitosis (mitotic index) and a minimum of 100 mitotic cells were evaluated for the frequency of numerical aberrations (polyploidy and endoreduplication). From each duplicate flask, 50 metaphases from separate slides were scored for structural chromosome aberrations by two independent evaluations. Only metaphases containing 21±2 chromosomes were evaluated. The two independent evaluations were combined to yield 100 metaphases per flask and 200 metaphases per concentration for structural chromosome aberrations. Applicants noted If these numbers were not attainable due to cytotoxicity or ≧50% aberrant metaphases observed in the first 25 metaphases/slide.

H. Statistical Data Analysis

The number and types of aberrations found, the percentage of structurally damaged cells (percent aberrant cells) in the total population of cells examined, and the mean aberrations per cell were calculated and reported for each treatment group. Chromatid and isochromatid gaps were presented in the data but are not included in the total percentage of cells with one or more aberrations or in the frequency of structural aberrations per cell. Statistical analysis of the frequency of aberrant cells (structural or numerical) was performed using the Fisher's exact test. The Fisher's test was used to compare pairwise the frequency of aberrant cells of each treatment group with that of the solvent control. In the event of a positive Fisher's exact test at any test article dose level, the Cochran-Armitage test was used to measure dose-responsiveness. As a guide to interpretation of the data, the test article was considered to induce a positive response when the percentage of cells with aberrations was increased in a dose-responsive manner with one or more concentrations being statistically significant ($p \leqq 0.05$). However, values that were statistically significant but do not exceed the range of historic negative or vehicle controls may be judged as not biologically significant. Test articles not demonstrating a statistically significant increase in aberrations were concluded to be negative.

I. Criteria for an Acceptable Assay

The full chromosome aberration assay was deemed acceptable if the following criteria were met:
1) The positive-control cultures must exhibit an increase in chromosome-aberration frequency that is statistically significant at the 5% level.
2) The percentage of damaged metaphases in the vehicle-control cultures must not exceed 6% (as an average).
3) The test article, at least at the highest dose, should exhibit some cytotoxicity (i.e., reduced in cell count or mitotic index). If no cytotoxicity was observed at the highest concentration, but the test article is either at the limit of solubility, or its dosing concentration limit (i.e., 10 mM or 5000 μg/ml), or its limit of volume (20%), the assay was considered acceptable.

J. Criteria for a Positive Response

The response to the test article was deemed positive if the following criteria are met:
1) Statistically significant (p<5%) increase in the percentage of aberrant cells was demonstrated using the Fisher's exact test.
2) A statistically significant (p<5%) increase in the chromosome aberration frequency was demonstrated in the Cochran-Armitage test used to measure dose-responsiveness.
3) The mean percent of damaged metaphases exceeded the upper limit of historical negative control levels (i.e., mean+2 standard deviations of the vehicle-control groups).

REFERENCES FOR THE CYTOGENIC SECTION

1. Snyder R D, and Green J W. A review of the genotoxicity of marketed pharmaceuticals, Mutation Research. 2001; 488: 151-169.
2. Evans H J. Cytological methods for detecting chemical mutagens. In: A. Hollaender editor. Chemical mutagens, principals and methods for their detection. New York and London, Plenum Press. 1976: vol. 4: 1-29.
3. Preston R J, Au W, Bender M A, Brewen J G, Carrano A V, Heddle J A, McFee A F, Wolff S and Wassom J S. Mammalian in-vivo and in-vitro cytogenetic assays: a report of the U.S. EPA's Gene-Tox Program. Mutation Res. 1981; 87: 143-188.
4. Galloway S M, Bloom A D, Resnick M, Margolin B H, Nakamura F, Archer P, and Zeiger E. Development of a standard protocol for in vitro cytogenetic testing in Chinese hamster ovary cells: Comparison of 22 compounds in two laboratories. Environ Mutagen. 1985; 7: 1-51.
5. Scott, D., Danford, N., Dean, B., Kirkland, D., and Richardson, C. In-vitro chromosome aberration assays. In B. J. Dean (ed.), Report of the UKEMS Sub-committee on Guidelines for Mutagenicity Testing, The United Kingdom Environmental Mutagen Society. 1983; 41-64.
6. OECD. Guidelines for testing chemicals: No. 473, In vitro mammalian chromosome aberration test: Organization for Economic Cooperation and Development, Paris, Adopted 21 Jul., 1997.
7. Swierenga S H H, Heddle J A, Sigal E A, Gilman J P W, Brillinger R L, Douglas G R and Nestmann E R. Recommended protocols based on a survey of current practice in genotoxicity testing laboratories, IV. Chromosome aberration and sister-chromatid exchange in Chinese hamster ovary, V79 Chinese lung and human lymphocyte cultures. Mutation Research. 1991; 246:301-322.
8. Galloway S M, Aardema M J, Ishidate Jr. M, Ivett J L, Kirkland D J, Morita T, Mosesso P, and Sofuni T. Report from working group on in vitro test for chromosome aberrations. Mutation Research. 1994; 312: 241-261.
9. Hillard C A, Armstrong M J, Bradt C I, Hill R B, Greenwood S K, and Galloway S M. Chromosome aberrations in vitro related to cytotoxicity of nonmutagenic chemicals and metabolic poisons. Environ Mol Mutagen. 1998; 31: 316-326.
10. Galloway S M. Cytotoxicity and chromosome aberrations in vitro: Experience in industry and the case for an upper limit on toxicity in the aberration assay. Environ Mol Mutagen. 2000; 35: 191-201.

The following abbreviations are employed herein:

Me=methyl

Et=ethyl

TBS=tert-butyldimethylsilyl

THF=tetrahydrofuran $Et_2O$=diethyl ether

EtOAc=ethyl acetate

DMF=dimethyl formamide

MeOH=methanol

EtOH=ethanol

DMAP=4-dimethylaminopyridine n-BuLi=n-butyllithium min=minute(s)

h or hr=hour(s)

L=liter mL=milliliter g=gram(s)

mg=milligram(s)

mol=moles mmol=millimole(s)

meq=milliequivalent sat or sat'd=saturated aq.=aqueous

TLC=thin layer chromatography

NMR=nuclear magnetic resonance

HPLC=high performance liquid chromatography

LC/MS=high performance liquid chromatography/mass spectrometry

MS or Mass Spec=mass spectrometry

Listed below are definitions of various terms used in the description of the instant invention. These definitions apply to the terms as they are used throughout the specification (unless they are otherwise limited in specific instances) either individually or as part of a larger group.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985); and c) *A Textbook of Drug Design and Development*, P. Krogsgaard-Larson and H. Bundgaard, eds. Ch 5, pgs 113-191 (Harwood Academic Publishers, 1991). Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compound of formula I of the invention can be prepared as shown in the following reaction Scheme 1 and description thereof, as well as relevant published literature procedures that may readily be used by one skilled in the art, without undue experimentation, to prepare the compounds described and claimed herein. Exemplary reagents and procedures for these reactions appear hereinafter in the working Example.

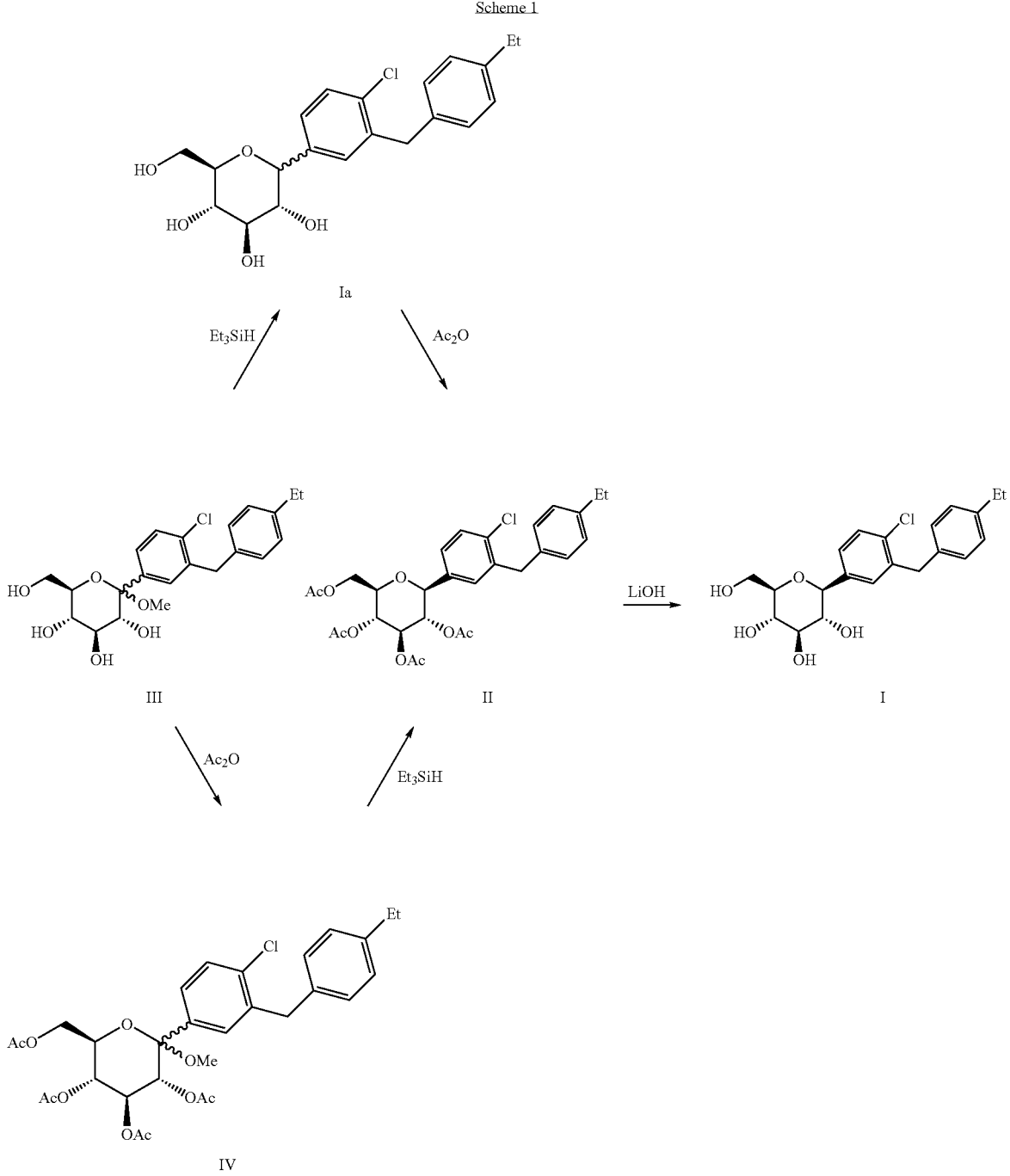

Compound of formula I can be prepared as shown in Scheme 1 by treatment of compound of formula II

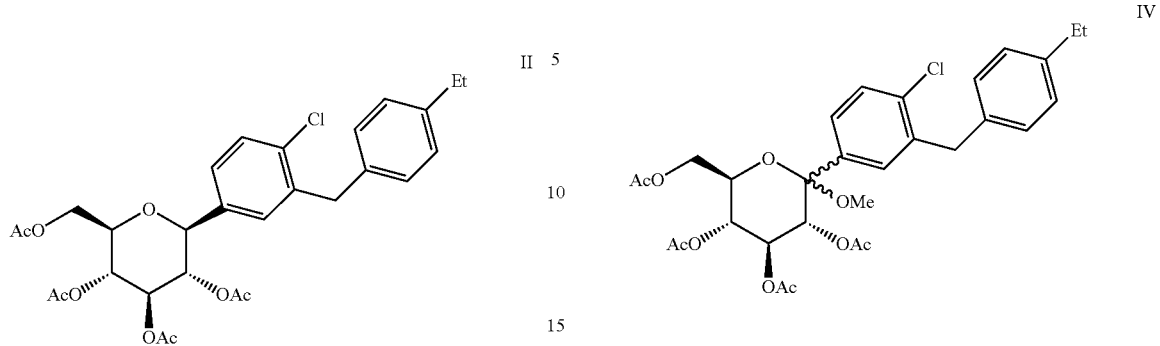

with a base such as LiOH or NaOH in a solvent such as a 1:2:3 mixture of H₂O/THF/MeOH or aq. MeOH or aq. EtOH.

Compound of formula II provides a convenient means to purify crude compound of formula Ia which was obtained as a mixture of alpha and beta anomers. Compound of formula II can be prepared by treatment of compound of formula Ia with Ac₂O in a solvent such as CH₂Cl₂ containing pyridine and a catalyst such as dimethylaminopyridine (DMAP).

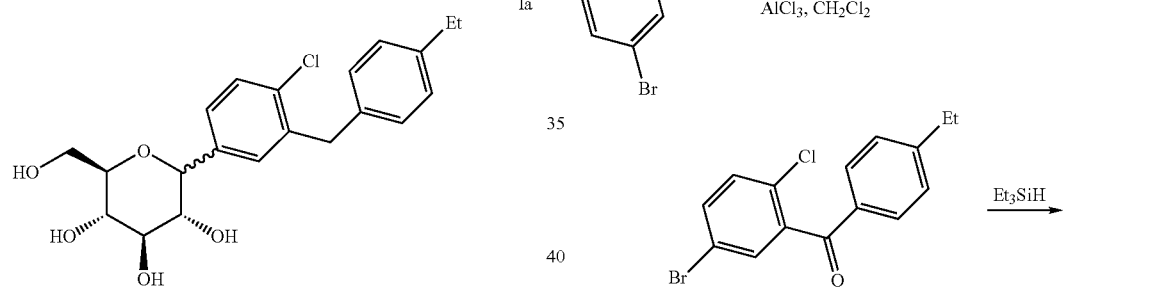

Compound of formula Ia can be prepared by reduction of a compound of formula III with a reducing agent such as Et₃SiH in a solvent such as 1:1 CH₂Cl₂/MeCN at −10° in the presence of a Lewis acid catalyst such as BF₃.Et₂O.

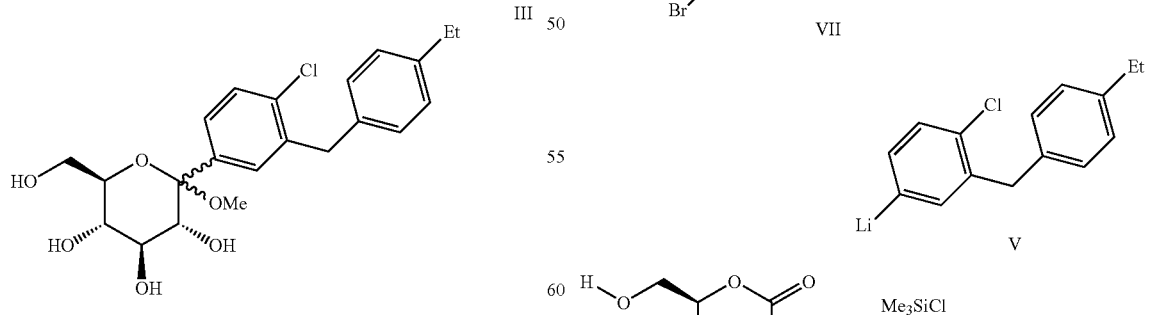

Compound of formula II can alternatively be prepared from compound of formula III by first acetylating compound of formula III with Ac₂O in a solvent such toluene or CH₂Cl₂ containing a base such as Hunig's base or Et₃N and a catalyst such as DMAP to generate compound of formula IV.

Subsequent conversion of compound of formula IV to compound of formula II can be achieved by treatment at 20° treatment with a reducing agent such as Et₃SiH in a solvent such as MeCN containing 1 equiv of H₂O and a Lewis acid catalyst such as BF₃.Et₂O.

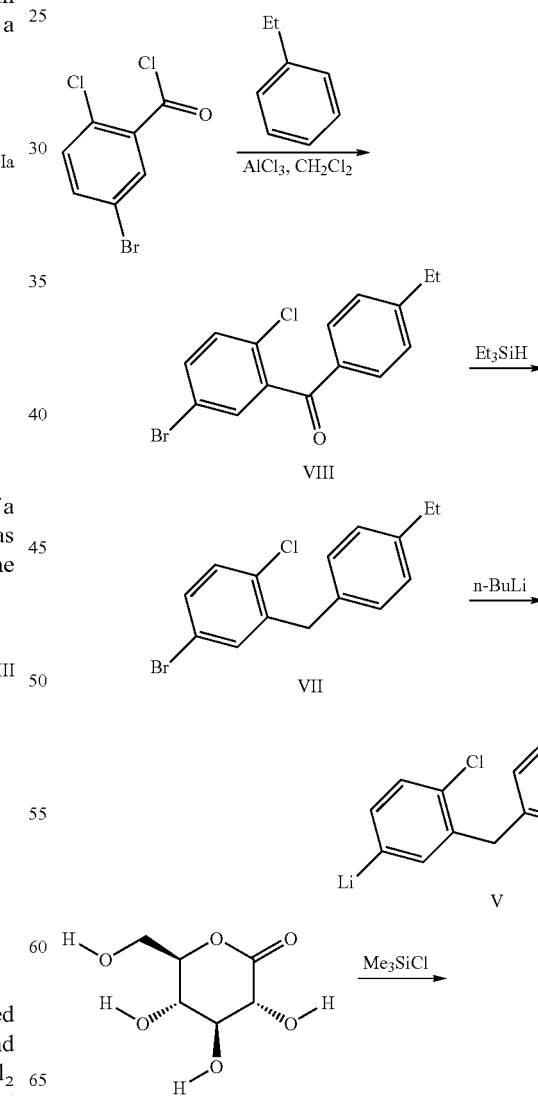

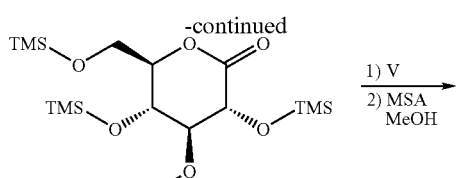

VI

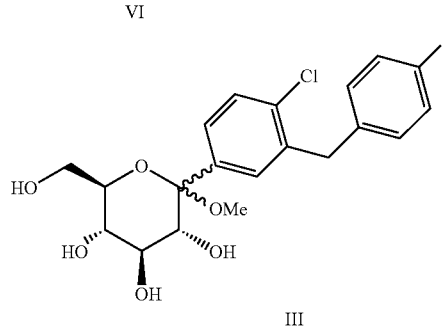

III

Compound of formula III can be prepared, as outlined in Scheme 2 above, by addition of a cold THF solution of an aryl lithium of formula V to a persilylated gluconolactone of formula VI in a solvent such as toluene at −75°. Subsequently, a methanol solution of a protic acid such methanesulfonic acid (MSA) was added after 30 min and the solution stirred at 20° until transformation of the intermediary lactol to III was complete.

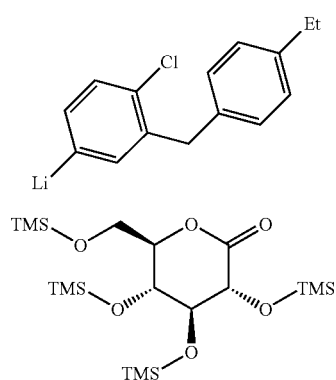

V

VI

Compound of formula VI can be prepared by treatment of commercially available D-gluconolactone with a silylating agent such as trimethylsilyl chloride in a solvent, such as THF, containing a base such as N-methylmorpholine.

Compound of formula V can be prepared by treatment of compound of formula VII with an alkyl lithium, such as n-BuLi or t-BuLi, in a solvent such as THF at −75°.

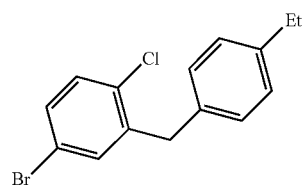

VII

Compound of formula VII can be readily prepared by treatment of compound of formula VIII with a reducing agent such as $Et_3SiH$ in a solvent such as TFA at 60° in the presence of a Lewis acid catalyst such as $BF_3.Et_2O$ or $CF_3SO_3H$.

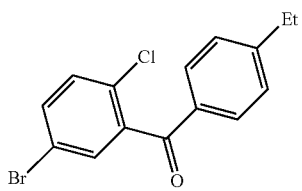

VIII

Compound of formula VIII can be prepared by Friedel-Craft acylation of commercially available ethylbenzene with 2-chloro-5-bromobenzoyl chloride in a solvent, such as ethylbenzene, containing an equivalent of a Lewis Acid, such as $AlCl_3$ or $AlBr_3$. 2-Chloro-5-bromobenzoyl chloride was readily prepared from commercially available 2-chloro-5-bromobenzoic acid by treatment with oxalyl chloride in a solvent, such as $CH_2Cl_2$, containing a catalytic amount of DMF.

Utilities and Combinations

A. Utilities

The compound of the present invention possesses activity as an inhibitor of the sodium dependent glucose transporters found in the intestine and kidney of mammals. Preferably, the compound of the invention is a selective inhibitor of renal SGLT2 activity, and therefore may be used in the treatment of diseases or disorders associated with SGLT2 activity.

Accordingly, the compound of the present invention can be administered to mammals, preferably humans, for the treatment of a variety of conditions and disorders, including, but not limited to, treating or delaying the progression or onset of diabetes (including Type I and Type II, impaired glucose tolerance, insulin resistance, and diabetic complications, such as nephropathy, retinopathy, neuropathy and cataracts), hyperglycemia, hyperinsulinemia, hypercholesterolemia, elevated blood levels of free fatty acids or glycerol, hyperlipidemia, hypertriglyceridemia, obesity, wound healing, tissue ischemia, atherosclerosis and hypertension. The compound of the present invention may also be utilized to increase the blood levels of high density lipoprotein (HDL).

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compound of the present invention.

B. Combinations

The present invention includes within its scope pharmaceutical compositions comprising, as an active ingredient, a therapeutically effective amount of a compound of formula I, alone or in combination with a pharmaceutical carrier or diluent. Optionally, the compound of the present invention can be utilized as an individual treatment, or utilized in combination with one or more other therapeutic agent(s).

Other "therapeutic agent(s)" suitable for combination with the compound of the present invention include, but are not limited to, known therapeutic agents useful in the treatment of the aforementioned disorders including: anti-diabetic agents;

anti-hyperglycemic agents; hypolipidemic/lipid lowering agents; anti-obesity agents; anti-hypertensive agents and appetite suppressants.

Examples of suitable anti-diabetic agents for use in combination with the compound of the present invention include biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) or other agonists of the GLP-1 receptor, and dipeptidyl peptidase IV (DPP4) inhibitors.

It is believed that the use of the compound of formula I in combination with at least one or more other antidiabetic agent(s) provides antihyperglycemic results greater than that possible from each of these medicaments alone and greater than the combined additive anti-hyperglycemic effects produced by these medicaments.

Other suitable thiazolidinediones include Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Examples of PPAR-alpha agonists, PPAR-gamma agonists and PPAR alpha/gamma dual agonists include muraglitizar, peliglitazar, AR-HO39242 (Astra/Zeneca), GW-409544 (Glaxo-Wellcome), GW-501516 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998), WO 01/21602 and in U.S. Pat. No. 6,653,314, the disclosure of which is incorporated herein by reference, employing dosages as set out therein, which compounds designated as preferred are preferred for use herein.

Suitable aP2 inhibitors include those disclosed in U.S. application Ser. No. 09/391,053, filed Sep. 7, 1999, and in U.S. application Ser. No. 09/519,079, filed Mar. 6, 2000, employing dosages as set out herein.

Suitable DPP4 inhibitors include those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540), 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996), the compounds disclosed in U.S. application Ser. No. 10/899,641, WO 01/868603 and U.S. Pat. No. 6,395,767, employing dosages as set out in the above references.

Other suitable meglitinides include nateglinide (Novartis) or KAD1229 (PF/Kissei).

Examples of suitable anti-hyperglycemic agents for use in combination with the compound of the present invention include glucagon-like peptide-1 (GLP-1) such as GLP-1(1-36) amide, GLP-1(7-36) amide, GLP-1(7-37) (as disclosed in U.S. Pat. No. 5,614,492), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671.

Examples of suitable hypolipidemic/lipid lowering agents for use in combination with the compound of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid co-transporter inhibitors, up-regulators of LDL receptor activity, bile acid sequestrants, cholesterol ester transfer protein (e.g., CETP inhibitors, such as CP-529414 (Pfizer) and JTT-705 (Akros Pharma)), PPAR agonists (as described above) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440.

The HMG CoA reductase inhibitors which may be employed in combination with one or more compound of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl]pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compound of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination the compound of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination the compound of formula I include those disclosed in Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an up-regulator of LD2 receptor activity, such as MD-700 (Taisho Pharmaceutical Co. Ltd) and LY295427 (Eli Lilly).

Examples of suitable cholesterol absorption inhibitor for use in combination with the compound of the invention include SCH48461 (Schering-Plough), as well as those disclosed in Atherosclerosis 115, 45-63 (1995) and J. Med. Chem. 41, 973 (1998).

Examples of suitable ileal Na$^+$/bile acid co-transporter inhibitors for use in combination with the compound of the invention include compounds as disclosed in Drugs of the Future, 24, 425-430 (1999).

The lipoxygenase inhibitors which may be employed in combination the compound of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compound of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compound of the present invention include a beta 3 adrenergic agonist, a lipase inhibitor, a serotonin (and dopamine) reuptake inhibitor, a thyroid receptor beta drug, 5HT2C agonists, (such as Arena APD-356); MCHR1 antagonists such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonsist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, a ciliary neurotrophic factor (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and/or an anorectic agent.

The beta 3 adrenergic agonists which may be optionally employed in combination with compound of the present invention include AJ9677 (Takeda/Dainippon), L750355

(Merck), or CP331648 (Pfizer) or other known beta 3 agonists, as disclosed in U.S. Pat. Nos. 5,541,204, 5,770,615, 5,491,134, 5,776,983 and 5,488,064.

Examples of lipase inhibitors which may be optionally employed in combination with compound of the present invention include orlistat or ATL-962 (Alizyme).

The serotonin (and dopoamine) reuptake inhibitor (or serotonin receptor agonists) which may be optionally employed in combination with a compound of the present invention may be BVT-933 (Biovitrum), sibutramine, topiramate (Johnson & Johnson) or axokine (Regeneron).

Examples of thyroid receptor beta compounds which may be optionally employed in combination with the compound of the present invention include thyroid receptor ligands, such as those disclosed in WO97/21993 (U. Cal SF), WO99/00353 (KaroBio) and GB98/284425 (KaroBio).

The monoamine reuptake inhibitors which may be optionally employed in combination with compound of the present invention include fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol.

The anorectic agent which may be optionally employed in combination with the compound of the present invention include topiramate (Johnson & Johnson), dexamphetamine, phentermine, phenylpropanolamine or mazindol.

The aforementioned patents and patent applications are incorporated herein by reference.

The above other therapeutic agents, when employed in combination with the compound of the present invention may be used, for example, in those amounts indicated in the Physician's Desk Reference, as in the patents set out above or as otherwise determined by one of ordinary skill in the art.

Where the compound of the invention are utilized in combination with one or more other therapeutic agent(s), either concurrently or sequentially, the following combination ratios and dosage ranges are preferred:

Where the other antidiabetic agent is a biguanide, the compound of formula I will be employed in a weight ratio to biguanide within the range from about 0.01:1 to about 100:1, preferably from about 0.1:1 to about 5:1.

The compound of formula I will be employed in a weight ratio to the glucosidase inhibitor within the range from about 0.01:1 to about 100:1, preferably from about 0.5:1 to about 50:1.

The compound of formula I will be employed in a weight ratio to the sulfonyl urea in the range from about 0.01:1 to about 100:1, preferably from about 0.2:1 to about 10:1.

The compound of formula I will be employed in a weight ratio to the thiazolidinedione in an amount within the range from about 0.01:1 to about 100:1, preferably from about 0.2:1 to about 10:1.

Where present, the thiazolidinedione anti-diabetic agent may be employed in amounts within the range from about 0.01 to about 2000 mg/day which may be administered in single or divided doses one to four times per day.

Optionally, the sulfonyl urea and thiazolidinedione may be incorporated in a single tablet with the compound of formula I in amounts of less than about 150 mg.

Where present, metformin or salt thereof may be employed in amounts within the range from about 500 to about 2000 mg per day which may be administered in single or divided doses one to four times daily.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The SGLT2 inhibitor of formula I will be employed in a weight ratio to the meglitinide, PPAR-gamma agonist, PPAR-alpha/gamma dual agonist, aP2 inhibitor or DPP4 inhibitor within the range from about 0.01:1 to about 100:1, preferably from about 0.2:1 to about 10:1.

The compound of formula I of the invention will be generally be employed in a weight ratio to the hypolipidemic agent (were present), within the range from about 500:1 to about 1:500, preferably from about 100:1 to about 1:100.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor in an amount within the range of from about 1 to 2000 mg, and preferably from about 4 to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

The squalene synthetase inhibitor may be employed in dosages in an amount within the range of from about 10 mg to about 2000 mg and preferably from about 25 mg to about 200 mg.

A preferred oral dosage form, such as tablets or capsules will contain the squalene synthetase inhibitor in an amount of from about 10 to about 500 mg, preferably from about 25 to about 200 mg.

The compound of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out a preferred method of the invention for treating any of the diseases disclosed herein, such as diabetes and related diseases, a pharmaceutical composition will be employed containing one or more of the compound of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compound can be administered to mammalian species including humans, monkeys, dogs, etc. by an oral route, for example, in the form of tablets, capsules, beads, granules or powders, or they can be administered by a parenteral route in the form of injectable preparations, or they can be administered intranasally or in transdermal patches. Typical solid formulations will contain from about 10 to about 500 mg of a compound of formula I. The dose for adults is preferably between 10 and 2,000 mg per day, which can be administered in a single dose or in the form of individual doses from 1-4 times per day.

A typical injectable preparation may be produced by aseptically placing 250 mg of compound of formula I into a vial, aseptically freeze-drying and sealing. For use, the contents of the vial are mixed with 2 mL of physiological saline, to produce an injectable preparation.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

SGLT2 inhibitor activity of the compound of the invention may be determined by use of an assay system as set out below.

Assay for SGLT2 Activity

The mRNA sequence for human SGLT2 (GenBank #M95549) was cloned by reverse-transcription and amplification from human kidney mRNA, using standard molecular biology techniques. The cDNA sequence was stably transfected into CHO cells, and clones were assayed for SGLT2 activity essentially as described in Ryan et al. (1994). Evaluation of inhibition of SGLT2 activity in a clonally selected cell line was performed essentially as described in Ryan et al., with the following modifications. Cells were plated at 10,000 or 20,000 cells per well and were cultured in Ham's F-12 medium containing 10% fetal bovine serum and 500 µg/ml geneticin. Cells at approximately 90% confluence were assayed 2 or 3 days after plating. Cells were washed once with buffer lacking sodium, which contained 10 mM Hepes/Tris, 137 mM N-methyl-D-glucamine, 5.4 mM KCl, 2.8 mM $CaCl_2$, and 1.2 mM $MgSO_4$, pH 7.4. Inhibitors were assayed in the presence of 10 µM [$^{14}$C] AMG (α-methyl-D-glucopyranoside) at 8 concentrations over a 120-minute incubation in protein-free buffer containing 10 mM Hepes/Tris, 137 mM NaCl, 5.4 mM KCl, 2.8 mM $CaCl_2$, and 1.2 mM $MgSO_4$, pH 7.4. The response curve was fitted to an empirical four-parameter model to determine the inhibitor concentration at half-maximal response, reported as the $IC_{50}$. Three replicates were performed per determination. Assays were quenched by washing 3 times in ice cold 1× phosphate buffered saline (PBS) containing 0.5 mM phlorizin, and cells were then lysed in 50 µl 0.1% NaOH. After addition of 200 µl MicroScint-40 scintillation fluid, the cells were allowed to shake for 1 hour, and then [$^{14}$C]AMG was quantified on a TopCount scintillation counter. Control assays in the absence of inhibitor were performed with and without NaCl and a dose response curve for phlorizin was generated in every assay as a positive control.

Ryan M J, Johnson G, Kirk J, Fuerstenberg S M, Zager R A and Torok-Storb B. 1994. HK-2: an immortalized proximal tubule epithelial cell line from normal adult human kidney. Kidney International 45: 48-57.

The following working Example serves to better illustrate, but not limit, embodiments of the present invention.

Example 1

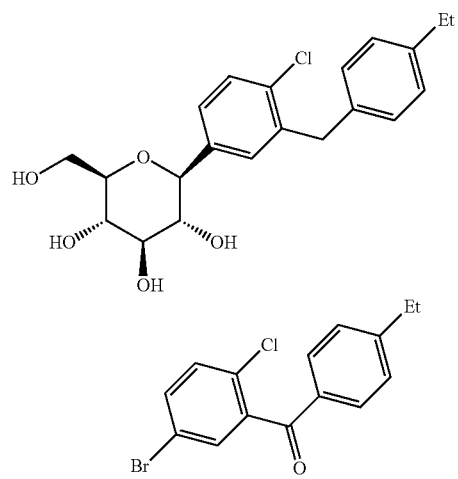

A. 5-Bromo-2-chloro-4'-ethylbenzophenone

To a 2 L round bottom flask containing a magnetic stirred suspension of commercial 5-bromo-2-chlorobenzoic acid (410 g, 1.74 mol) in 700 mL of $CH_2Cl_2$ was added oxalyl chloride (235 g, 1.85 mol) followed by 1.5 mL of DMF. To trap the resultant HCl, the flask was fitted with tubing so that the gas was discharged above the surface of a stirred aq KOH solution. When the vigorous evolution of gas ceased after two hours, the homogeneous reaction was stirred overnight prior to removal of the volatiles under vacuum using a rotary evaporator. The resultant oil solidified during subsequent evacuation.

After dissolving the crude 5-bromo-2-chlorobenzoyl chloride in 530 ml of ethylbenzene, the yellow solution was cooled to −3° C. prior to adding $AlCl_3$ (257 g, 1.93 mol) in ~30 g portions over 60 min to insure that the temperature did not exceed 10° C. The copious amounts of HCl gas which began to evolve after 60% of the $AlCl_3$ had been added were trapped by passing the gas over a stirred conc. NaOH solution. If the reaction were more concentrated, a magnetic stirrer could not have maintained stirring upon completion of the addition of $AlCl_3$. After stirring for 1 hr as the bath warmed to ~15° C., the bath was removed. After 4 hr at 20° C., the thick syrup was poured over ice (1.5 kg). Subsequently, once the stirred suspension had cooled, $H_2O$ (1 L) was added prior to being extracted 4× with EtOAc. The combined organic extracts were washed 2× with 1N HCl, 3× with 1M KOH, and 2× with brine prior to drying over $Na_2SO_4$. The volatiles were removed using first a rotary evaporator and then by heating at ~60° C. at 1 Torr. $^1$H NMR analysis of the resultant dark oil revealed the residue to be a 1:14 mixture of ortho/para isomers. Dissolution in hexane and followed by filtration through a silica gel pad removed most of the color. Concentration of the eluent yielded 560 g (99%) of a 14:1 mixture of 5-bromo-2-chloro-4'-ethylbenzophenone/5-bromo-2-chloro-2'-ethylbenzophenone.

HPLC retention time: 4.7 min, YMC S5 C-18 4.6×50 mm column, 2.5 mL/min, detection at 220 nM; 4 min gradient 0-100% B hold 2 min at 100% B. Solvent A: 10% MeOH/H$_2$O+0.2% H$_3$PO$_4$. Solvent B: 90% MeOH/H$_2$O+0.2% H$_3$PO$_4$.

5-Bromo-2-chloro-4'-ethylbenzophenone $^1$H NMR (400 MHz, CDCl$_3$) δ 7.73 (d, 2H, J$_{AB}$=8.2 Hz), 7.54 (dd, 1H, J=2.2 Hz, J=8.8 Hz), 7.32 (d, 1H, J=8.8 Hz), 7.295 (d, 2H, J$_{AB}$=8.2 Hz), 2.72 (q, 2H, J=7.7 Hz), 1.27 (t, 3H, J=7.7 Hz).
$^{13}$C NMR (100 MHz, CDCl$_3$) δ 193.13. 151.33, 140.49, 133.8, 133.52, 131.6, 131.44, 130.34, 130.16, 128.28, 120.44, 29.04, 15.02.

5-Bromo-2-chloro-2'-ethylbenzophenone (distinctive signals)

$^1$H NMR (400 MHz, CDCl$_3$) δ 2.64 (q, 2H, J=7.7 Hz), 1.23 (t, 3H, J=7.7 Hz).
$^{13}$C NMR (100 MHz, CDCl$_3$) δ 28.9, 15.5.

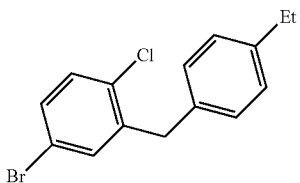

B. 5-Bromo-2-chloro-4'-ethyldiphenylmethane

To a stirred solution of Et$_3$SiH (400 g, 3.45 mol and 5-bromo-2-chloro-4'-ethylbenzophenone (534 g, 1.65 mol) containing ~7% of the isomeric ketone in 300 mL of TFA at 30° C. was added CF$_3$SO$_3$H (1.5 g, 0.01 mol). Within minutes the temperature increased causing the solution to reflux violently. Caution this moderate exotherm requires cooling with an external ice bath. After 1 hr, HPLC revealed the reaction to be 90% complete. After addition of an additional Et$_3$SiH (20 g) and heating overnight at 70° C., the reaction was >95% complete by HPLC analysis. Upon cooling, the volatiles were removed by bulb to bulb distillation at reduced pressure. The resultant ~1 L of light gray oil was poured into 1 L of H$_2$O. The mixture was extracted 3× with hexane; the combined organic layers were washed 3× with H$_2$O, 2× with aq Na$_2$CO$_3$ and 2× with brine before drying over Na$_2$SO$_4$. After concentration using a rotary evaporator, ~1 L of clear light amber oil remained. This material was further concentrated; the (Et$_3$Si)$_2$O (450 mL) was removed by distillation at 0.6 Torr. Once the temperature at the distillation head reached 75° C., the pot was allowed to cool. $^1$H NMR analysis of the pot revealed it to contain an ~8:1 mixture of diarylmethane to (Et$_3$Si)$_2$O. Crystallization of this mixture was achieved by pouring the product into vigorously stirred 10° C. 85% EtOH/H$_2$O (1.2 L), After stirring for several hours, the crystals were collected by filtration, washed with cold 1:1 EtOH/H$_2$O and dried under vacuum. The 5-bromo-2-chloro-4'-ethyldiphenyl-methane (500 g), obtained as a low melting solid containing ~1% (Et$_3$Si)$_2$O, was used without further purification.

HPLC retention time: 5.3 min, YMC S5 C-18 4.6×50 mm column, 2.5 mL/min, detection at 220 nM; 4 min gradient 0-100% B hold 2 min at 100% B. Solvent A: 10% MeOH/H$_2$O+0.2% H$_3$PO$_4$. Solvent B: 90% MeOH/H$_2$O+0.2% H$_3$PO$_4$.

$^1$H NMR (125 MHz, CDCl$_3$) δ 7.27-7.23 (m, 3H), 7.14 (d, 2H, J$_{AB}$=7.7 Hz), 7.09 (d, 2H, J$_{AB}$=7.7 Hz), 2.63 (q, 2H, J=7.7 Hz), 1.23 (t, 3H, J=7.7 Hz).
$^{13}$C NMR (100 MHz, CDCl$_3$) δ 142.46. 141.08, 135.68, 133.64, 133.13, 130.85, 130.55, 128.83, 128.1, 120.0, 38.62, 28.43, 15.51.

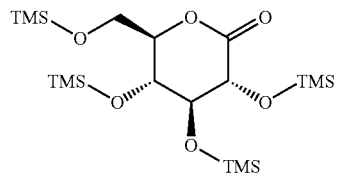

C. 2,3,4,6-tetra-O-Trimethylsilyl-D-glucolactone

To a stirred −5° C. solution of gluconolactone (239 g, 1.34 mol) and N-methylmorpholine (1180 mL, 10.73 mol) in 2.4 L of THF under Ar was added trimethylsilyl chloride (1022 mL, 8.05 mol) via dropping funnel at a rate such that the temperature did not exceed 5° C. After 1 hr the stirred reaction was heated to 35° C. for 5 hr whereupon it was allowed to cool to 20° C. as the reaction stirred overnight. After dilution with 3.6 L of toluene, the mixture was cooled to 0-5° C. prior to cautiously adding 7 L of H$_2$O at a rate such that the temperature did not exceed 10° C. Note a severe exotherm results upon addition of the first portion of H$_2$O. After mixing, the phases were allowed to separate and then split. The organic phase was washed with aq. NaH$_2$PO$_4$ (2 L), H$_2$O (1 L), and brine (1 L). The organic layer was then concentrated under vacuum using a rotary evaporator; the resultant light yellow oil was twice taken up 250 mL of toluene and reconcentrated to yield 616 g.

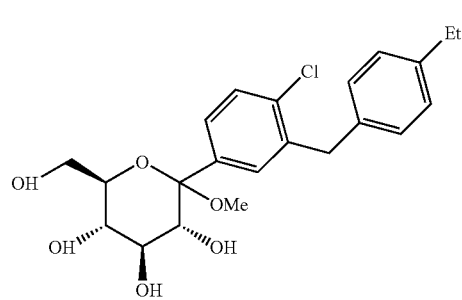

D

To a stirred −780 solution of Part B 5-bromo-2-chloro-4'-ethyldiphenylmethane (88 g, 0.28 mol) in 450 mL of 1:2 dry THF/toluene under Ar was slowly added 2.5 M n-BuLi (136 mL, 0.34 mol) in hexane at a rate that maintained the temperature below −55°. After stirring for 10 minutes following the addition, this solution was transferred by cannula to a stirred −78° solution of Part C 2,3,4,6-tetra-O-trimethylsilyl-D-glucolactone (153 g, 0.33 mol) in toluene (350 mL) at a rate that maintained the reaction below −55°. The solution was stirred for 30 min at −78° prior to quenching by addition of 400 mL of MeOH containing methanesulfonic acid (28 mL, 0.45 mol). The reaction was stirred overnight for 18 hr at 20° C. The reaction was stirred overnight for 18 hr at 20° C. HPLC analysis revealed a new peak which by LC/MS correspond to the mass of the expected O-methylglucoside. The reaction, once complete, was quenched by the addition of NaHCO$_3$ (42 g, 0.5 mol) in 200 mL of $H_2O$. If the pH was not weakly basic, more $NaHCO_3$ was added prior to dilution 2 fold with $H_2O$ and 3 extractions with EtOAc. The combined EtOAc fractions were washed with brine and dried over $Na_2SO_4$. After concentration using a rotary evaporator, the oil (140 g, 90% pure by HPLC analysis) was not further purified but instead was carried forward as an impure diastereomeric mixture.

$^1H$ NMR (400 MHz, $CDCl_3$) δ 7.37 (m, 1H), 7.23 (m, 2H), 7.02 (m, 4H), 5.14 (m, 1H), 5.06 (m, 1H), 4.07 (m, 1H), 4.03 (d, 1H, $J_{AB}$=15.4 Hz), 3.97 (d, 1H, $J_{AB}$=15.4 Hz), 3.80-3.70 (m, 4H), 3.60 (m, 1H), 3.48 (m, 1H), 3.31 (m, 1H), 2.84 (s, 3H), 2.53 (q, 2H, J=7.5 Hz), 1.14 (t, 3H, J=7.5 Hz).

$^{13}C$ NMR (100 MHz, $CDCl_3$) δ 144.4, 140.7, 138.94, 136.9, 132.51, 131.6, 130.96, 130.6, 130.2, 129.16, 103.36, 77.0, 74.86, 72.48, 64.27, 51.57, 41.33, 30.75, 17.9.

HPLC retention time: 4.28 min, 90% pure, YMC S5 C-18 4.6×50 mm column, 2.5 mL/min, detection at 220 nM; 4 min gradient 0-100% B hold 2 min at 100% B. Solvent A: 10% $MeOH/H_2O$+0.2% $H_3PO_4$. Solvent B: 90% $MeOH/H_2O$+ 0.2% $H_3PO_4$.

LC/MS: [M-OMe]$^+$391, 393; [M+Na]$^+$445, 447.

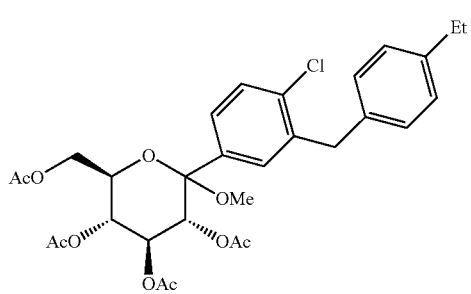

E

A solution of Part D O-methylglucoside (206 g, 0.49 mol) in THF (1 L) containing diisopropylethylamine (465 g, 3.6 mol) and DMAP (0.5 g, 4.1 mmol) was cooled to 0° C. Acetic anhydride (326 g, 3.19 mol) was slowly added at such a rate that the temperature did not exceed 5° C. After the solution gradually warmed to 20° C., it was stirred for 10 hours whereupon tlc analysis revealed complete conversion to the tetraacetate. The reaction was quenched by addition of EtOAc (1.5 L) and 10% aq. $H_3PO_4$ (1.5 L). After separation of the layers, the aq. phase was extracted 2× with EtOAc. The combined organic phases were washed 1× with brine prior to drying over $Na_2SO_4$ and concentration under vacuum. The resultant oil was dissolved twice in 300 mL of toluene and reconcentrated to yield a thick oil (300 g, 95% HPLC purity) that was used without further purification of the resulting impure diastereomeric mixture.

$^1H$ NMR (400 MHz, $CDCl_3$) δ 7.38 (d, 1H, J=8.3 Hz), 7.28 (dd, 1H, J=8.3 Hz, J=2.2 Hz), 7.24 (d, 1H, J=2.2 Hz), 7.11 (d, 2H, $J_{AB}$=8.3 Hz), 7.04 (d, 2H, $J_{AB}$=8.3 Hz), 5.56 (t, 1H, J=9.7 Hz), 5.21 (t, 1H, J=10.1 Hz), 4.93 (t, 1H, J=10.1 Hz), 4.20 (dd, 1H, J=12 Hz, J=2 Hz), 4.12 (d, 1H, $J_{AB}$=15.4 Hz), 4.02 (m, 1H), 4.018 (d, 1H, $J_{AB}$=15.4 Hz), 3.10 (s, 3H), 2.606 (q, 2H, J=7.7 Hz), 2.097 (s, 3H), 2.05 (s, 3H), 1.94 (s, 3H), 1.72 sd (s, 3H), 1.21 (t, 3H, J=7.7 Hz).

$^{13}C$ NMR (100 MHz, $CDCl_3$) δ 170.7, 170.05, 169.47, 168.9, 142.2, 138.74, 136.4, 135.1, 134.7, 129.8, 129.4, 128.6, 128.0, 126.0, 100.02, 73.83, 71.33, 68.87, 68.77, 62.11, 49.43, 38.75, 28.4, 22.64, 20.68, 20.58, 20.16, 15.5.

HPLC retention time: 4.81 min, 90% pure, YMC S5 C-18 4.6×50 mm column, 2.5 mL/min, detection at 220 nM; 4 min gradient 0-100% B hold 2 min at 100% B. Solvent A: 10% $MeOH/H_2O$+0.2% $H_3PO_4$. Solvent B: 90% $MeOH/H_2O$+ 0.2% $H_3PO_4$.

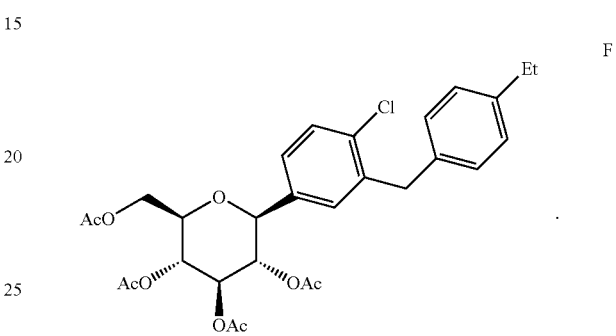

F

A stirred solution of the above crude oil (301 g, 0.51 mol) in $CH_2Cl_2$ (500 mL) containing one equivalent of $H_2O$ (9 g, 0.5 mol) and $Et_3SiH$ (188 g, 1.62 mol) was cooled to −20° C. prior to addition of $BF_3.Et_2O$ (145 g, 1.02 mol). During the addition, the temperature was maintained <0° C. The reaction was subsequently stirred 2 hr at 10° C. and 18 hr at 15-20° C. before being quenched by addition of $CH_2Cl_2$ (500 mL) and $H_2O$ (500 mL). After separation of the layers, the aq phase was extracted once with $CH_2Cl_2$. The combined organic layers were washed 1× with aq $NaHCO_3$ and brine prior to drying over $Na_2SO_4$. After removal of the $Na_2SO_4$ by filtration, $Ac_2O$ (6.4 g, 65 mmol), diisopropylethylamine (9.5 g, 74 mmol) and DMAP (100 mg, 0.8 mmol) were added. The solution was stirred at 20° C. for 18 hr to insure that any glucoside hydroxyls that hydrolyzed during the reduction and work-up were reacetylated. The oil, obtained after concentration under vacuum, crystallized upon addition of EtOH. After filtration the purity of this material by HPLC was 98%; recrystallization from EtOH yielded the tetraacetylated beta-C-glucoside as a white solid (180 g, 99.8% purity. The overall conversion for procedures D-F was 61%.

HPLC retention time: 4.74 min, 100% pure, YMC S5 C-18 4.6×50 mm column, 2.5 mL/min, detection at 220 nM; 4 min gradient 0-100% B hold 2 min at 100% B. Solvent A: 10% $MeOH/H_2O$+0.2% $H_3PO_4$. Solvent B: 90% $MeOH/H_2O$+ 0.2% $H_3PO_4$.

$^1H$ NMR (500 MHz, $CDCl_3$) δ 7.35 (d, 1H, J=8.2 Hz), 7.19 (dd, 1H, J=8.2 Hz, J=2.2 Hz), 7.11 (d, 2H, $J_{AB}$=8.5 Hz), 7.086 (d, 1H, J=2.2 Hz), 7.06 (d, 2H, $J_{AB}$=8.5 Hz), 5.28 (t, 1H, J=9.7 Hz), 5.20 (t, 1H, J=9.7 Hz), 5.04 (t, 1H, J=9.7 Hz), 4.31 (d, 1H, J=9.9 Hz), 4.26 (dd, 1H, J=12 Hz, J=5 Hz), 4.135 (dd, 1H, J=12 Hz, J=5 Hz), 4.095 (d, 1H, $J_{AB}$=7.7 Hz), 3.995 (d, 1H, $J_{AB}$=7.7 Hz), 3.79 (m, 1H), 2.605 (q, 2H, J=7.7 Hz), 2.069 (s, 3H), 2.04 (s, 3H), 1.98 (s, 3H), 1.67 (s, 3H), 1.21 (t, 3H, J=7.7 Hz).

$^{13}$C NMR (125 MHz, CDCl$_3$) δ 170.64, 170.3, 169.4, 168.7, 142.2, 138.78, 136.4, 135.1, 134.6, 129.9, 129.8, 128.7, 128.0, 125.9, 79.45, 76.1, 74.1, 72.5, 68.45, 62.2, 38.6, 28.4, 20.7, 20.6, 20.59, 20.2, 15.55.

LC-MS [M+NH$_4^+$] at m/z 578.3

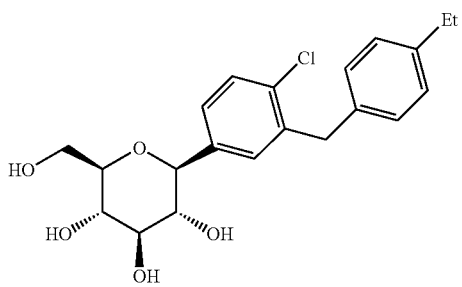

G

To the white suspension formed by stirring the tetraacetylated beta-C-glucoside of Part F (25 g, 44.6 mmol) for 5 min in 2:3 THF/MeOH (350 mL) under N$_2$ at 20° C. was added LiOH.H$_2$O (2.0 g, 50 mmol) in H$_2$O (70 mL). After 15 min, the reaction was an opaque solution; after 2.5 hr, by HPLC analysis the reaction was 98% complete. The conversion increased to 99% after stirring overnight whereupon the volatiles were removed using a rotary evaporator such that the volume was reduced to 150 mL. The residue, after addition of 10% aq KHSO$_4$ (100 mL) was further diluted with 100 mL of H$_2$O prior to being extracted 3× with EtOAc. After drying over Na$_2$SO$_4$, the volatiles were removed using a rotary evaporator and the resultant oil in the minimum amount of EtOAc foamed under vacuum. The amount of EtOAc trapped in this material can be reduced by drying under vacuum. This glassy off white solid was scraped out and further dried at 0.15 Torr at 25° C. for 24 hr to yield 17.3 g of desired C-arylglucoside containing 6.7 mol % of EtOAc.

HPLC retention time: 4.21 min, 98.8% pure, YMC S5 C-18 4.6×50 mm column, 2.5 mL/min, detection at 220 nM; 4 min gradient 0-100% B hold 2 min at 100% B. Solvent A: 10% MeOH/H$_2$O+0.2% H$_3$PO$_4$. Solvent B: 90% MeOH/H$_2$O+ 0.2% H$_3$PO$_4$.

$^1$H NMR (500 MHz, CD$_3$OD) δ 7.34 (d, 1H, J=8.2 Hz), 7.33 (d, 1H, J=1.7 Hz), 7.27 (dd, 1H, J=8.2 Hz, J=1.7 Hz), 7.08 (partially superimposed AB quartet, 4H), 4.1-4.0 (m, 3H), 3.86 (d, 1H, J=11.6 Hz), 3.68 (dd, 1H, J=5.3, 10.6 Hz), 3.46-3.26 (m, 4H) Hz), 2.57 (q, 2H, J=7 Hz), 1.19 (t, 3H, J=7 Hz).

$^{13}$C NMR (125 MHz, CD$_3$OD) δ 143.2, 140.0, 139.7, 138.1, 134.5, 131.98, 130.1, 129.8, 128.8, 128.2, 82.8, 82.14, 79.7, 76.4, 71.9, 63.1, 39.7, 29.4, 16.25.

MS [M+Na$^+$] at m/z Theoretical 415.1288; Observed 415.1293

Anal for C$_{21}$H$_{25}$ClO$_5$.0.07 EtOAc.0.19H$_2$O Calcd C, 63.51; H, 6.50; Cl, 8.80. Found C, 63.63; H, 6.63; Cl, 8.82.

What is claimed:

1. A compound of formula I

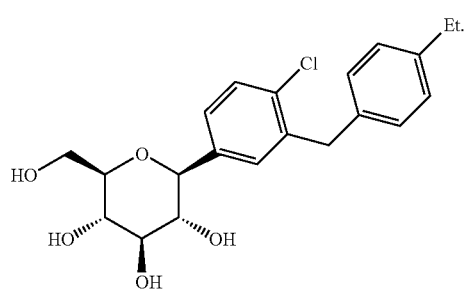

2. A pharmaceutical composition comprising a compound of formula I having the structure

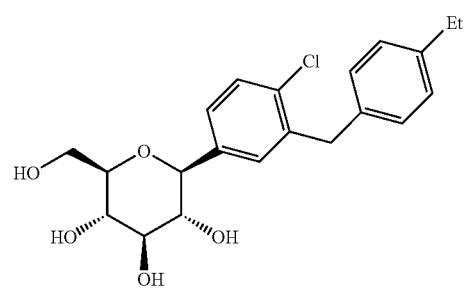

and a pharmaceutically acceptable carrier therefor.

3. A pharmaceutical combination comprising a compound of formula I having the structure

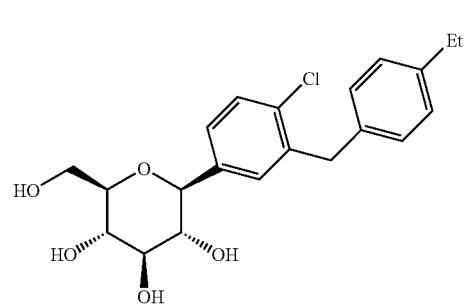

and at least one therapeutic agent selected from the group consisting of an antidiabetic agent, an anti-obesity agent, an anti-hypertensive agent, an anti-atherosclerotic agent and a lipid-lowering agent.

4. The pharmaceutical combination as defined in claim 3 comprising the compound of formula I and at least one antidiabetic agent.

5. The combination as defined in claim 4 wherein the antidiabetic agent is at least one agent selected from the group consisting of a biguanide, a sulfonyl urea, a glucosidase inhibitor, a PPAR gamma agonist, a PPAR alpha/gamma dual agonist, an aP2 inhibitor, a DPP4 inhibitor, an insulin sensitizer, a glucagon-like peptide-1 (GLP-1), a PTP1B inhibitor, a glycogen phosphorylase inhibitor, a glucose-6-phosphatase inhibitor, insulin and a meglitinide.

6. The combination as defined in claim 4 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, isaglitazone, repaglinide, nateglinide, muraglitizar and peliglitazar.

7. The combination as defined in claim 4 wherein the compound of formula I is present in a weight ratio to the antidiabetic agent within the range from about 0.01 to about 300:1.

8. The combination as defined in claim 3 wherein the anti-obesity agent is at least one agent selected from the group consisting of a beta 3 adrenergic agonist, a lipase inhibitor, a serotonin reuptake inhibitor, a thyroid receptor beta drug, a 5HT2C agonist, an MCHR1 antagonist, a melanocortin receptor agonist, a melanin-concentrating hormone receptor antagonist, a galanin receptor modulator, an aorexin antagonist, a CCK agonists, an NPY1 or NPY5 antagonist, an NPY2 or NPY4 modulator, a corticotropin releasing factor agonist, a histamine receptor-3 (1-13) modulator, a 11-beta-HSD-1 inhibitor, a adinopectin receptor modulator, a monoamine reuptake inhibitor, a ciliary neurotrophic factor, a brain-derived neurotrophic factor, leptin or leptin receptor modulators, a cannabinoid-1 receptor antagonist and an anorectic agent.

9. The combination as defined in claim 8 wherein the anti-obesity agent is at least one agent selected from the group consisting of rimonabant, orlistat, sibutramine, topiramate, dexamphetamine, phentermine, phenylpropanolamine and mazindol.

10. The combination as defined in claim 3 wherein the lipid lowering agent is at least one agent selected from the group consisting of an MTP inhibitor, a CETP inhibitor, an HMG CoA reductase inhibitor, a squalene synthetase inhibitor, a fibric acid derivative, an upregulator of LDL receptor activity, a lipoxygenase inhibitor and an ACAT inhibitor.

11. The combination as defined in claim 10 wherein the lipid lowering agent is at least one agent selected from the group consisting of pravastatin, lovastatin, simvastatin, atorvastatin, cerivastatin, fluvastatin, nisvastatin, visastatin, atavastatin, rosuvastatin, fenofibrate, gemfibrozil, clofibrate and avasimibe.

12. The combination as defined in claim 10 wherein the compound of formula I is present in a weight ratio to the lipid-lowering agent within the range from about 0.01 to about 300:1.

13. A method for treating or delaying the progression or onset of diabetes, diabetic retinopathy, diabetic neuropathy, diabetic nephropathy, delayed wound healing, insulin resistance, hyperglycemia, hyperinsulinemia, elevated blood levels of fatty acids or glycerol, hyperlipidemia, obesity, hypertriglyceridemia, Syndrome X, diabetic complications, atherosclerosis or hypertension, or for increasing high density lipoprotein levels, comprising administering a therapeutically effective amount of a compound of formula I

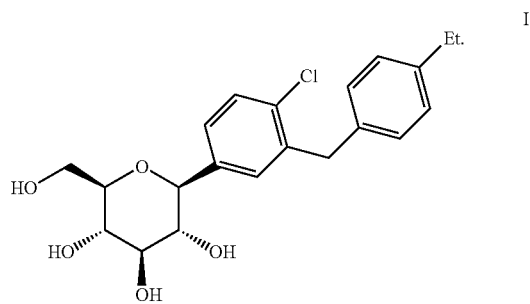

14. The method of claim 13 further comprising administering, concurrently or sequentially, a therapeutically effective amount of at least one additional therapeutic agent selected from the group consisting of an antidiabetic agent, an anti-obesity agent, a anti-hypertensive agent, an anti-atherosclerotic agent and a lipid-lowering agent.

15. A method for treating type II diabetes comprising administering a therapeutically effective amount of a compound of formula I

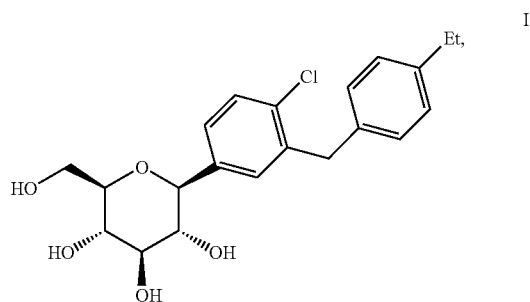

alone or in combination with at least one other therapeutic agent selected from the group consisting of antidiabetic agent, an agent for treating the complications of diabetes, an anti-obesity agent, an antihypertensive agent, an antiplatelet agent, an anti-atherosclerotic agent and a hypolipidemic agent.

* * * * *

UNITED STATES PATENT AND TRADEMARK OFFICE
CERTIFICATE OF CORRECTION

| | | |
|---|---|---|
| PATENT NO. | : 7,589,193 B2 | Page 1 of 1 |
| APPLICATION NO. | : 11/233617 | |
| DATED | : September 15, 2009 | |
| INVENTOR(S) | : Washburn et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C 154(b) by 790 days.

Signed and Sealed this
Eighteenth Day of January, 2011

David J. Kappos
*Director of the United States Patent and Trademark Office*

UNITED STATES PATENT AND TRADEMARK OFFICE
CERTIFICATE OF CORRECTION

PATENT NO.        : 7,589,193 B2
APPLICATION NO.   : 11/233617
DATED             : September 15, 2009
INVENTOR(S)       : William Washburn et al.

It is certified that error appears in the above-identified patent and that said Letters Patent is hereby corrected as shown below:

In the Claims:

Claim 6:

Column 31, line 4, change "muraglitizar" to -- muraglitazar --.

Claim 8:

Column 31, line 15, change "aorexin" to -- orexin --.

Column 31, line 18, change "(1-13)" to -- (H3) --.

Column 31, line 19, change "adinopectin" to -- adiponectin --.

Signed and Sealed this
Twenty-fifth Day of October, 2011

David J. Kappos
*Director of the United States Patent and Trademark Office*